(12) United States Patent
Schlaeper et al.

(10) Patent No.: US 8,449,686 B2
(45) Date of Patent: May 28, 2013

(54) METHODS FOR CLEANING A DRAIN LINE OF A DIALYSIS MACHINE

(75) Inventors: Christian Schlaeper, Concord, CA (US); Martin Joseph Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 574 days.

(21) Appl. No.: 12/767,417

(22) Filed: Apr. 26, 2010

(65) Prior Publication Data

US 2011/0259371 A1 Oct. 27, 2011

(51) Int. Cl.
*B08B 9/032* (2006.01)
(52) U.S. Cl.
USPC .......... 134/22.11; 134/22.12; 134/22.18; 134/26; 134/34
(58) Field of Classification Search
None
See application file for complete search history.

(56) References Cited

U.S. PATENT DOCUMENTS

| | | | |
|---|---|---|---|
| 3,871,913 A | 3/1975 | Shaldon | |
| 4,174,231 A | 11/1979 | Hobgood | |
| 4,191,351 A | 3/1980 | Goyne | |
| 4,581,141 A | 4/1986 | Ash | |
| 4,666,598 A | 5/1987 | Heath et al. | |
| 4,684,460 A | 8/1987 | Issautier | |
| 4,728,496 A | 3/1988 | Petersen et al. | |
| 4,770,787 A | 9/1988 | Heath et al. | |
| 4,784,495 A | 11/1988 | Jonsson et al. | |
| 4,789,467 A | 12/1988 | Lindsay et al. | |
| 4,997,577 A | 3/1991 | Stewart | |
| 5,256,371 A | 10/1993 | Pippert | |
| 5,262,068 A | 11/1993 | Bowers et al. | |
| 5,277,820 A | 1/1994 | Ash | |
| 5,304,349 A | 4/1994 | Polaschegg | |
| 5,409,612 A | 4/1995 | Maltais et al. | |
| 5,421,813 A | 6/1995 | Ohnishi | |
| 5,536,412 A | 7/1996 | Ash | |
| 5,589,070 A | 12/1996 | Maltais et al. | |
| 5,591,344 A | 1/1997 | Kenley et al. | |
| 5,603,902 A | 2/1997 | Maltais et al. | |
| 5,605,630 A | 2/1997 | Shibata | |
| 5,713,125 A | 2/1998 | Watanabe et al. | |
| 5,788,099 A | 8/1998 | Treu et al. | |
| 5,919,369 A | 7/1999 | Ash | |

(Continued)

FOREIGN PATENT DOCUMENTS

| | | |
|---|---|---|
| EP | 0 278 100 | 8/1988 |
| EP | 0 673 658 | 9/1995 |

(Continued)

OTHER PUBLICATIONS

"*RX Guide to Custom Dialysis*," COBE Renal Care Inc., Revision E. Sep. 1993.

(Continued)

*Primary Examiner* — Michael Barr
*Assistant Examiner* — Ryan Coleman
(74) *Attorney, Agent, or Firm* — Fish & Richardson P.C.

(57) ABSTRACT

A method for cleaning a drain line of a dialysis machine downstream of a filtration unit. The method includes closing inlet and outlet valves of the filtration unit, and closing a bypass valve along a bypass line that connects a source line to a drain line. The method also includes configuring the balancing chamber such that flow is permitted only via the drain line, flowing an amount of a cleaning agent into the drain line through a cleaning agent valve, and rinsing the cleaning agent from the drain line with a rinse fluid.

13 Claims, 6 Drawing Sheets

U.S. PATENT DOCUMENTS

| | | |
|---|---|---|
| 5,944,684 A | 8/1999 | Roberts et al. |
| 6,000,567 A | 12/1999 | Carlsson et al. |
| 6,036,858 A | 3/2000 | Carlsson et al. |
| 6,086,753 A | 7/2000 | Ericson et al. |
| 6,143,181 A | 11/2000 | Falkvall et al. |
| 6,170,785 B1 | 1/2001 | Lampropoulos |
| 6,190,855 B1 | 2/2001 | Herman et al. |
| 6,277,277 B1 | 8/2001 | Jacobi et al. |
| 6,280,632 B1 | 8/2001 | Polaschegg |
| 6,308,721 B1 | 10/2001 | Bock et al. |
| 6,409,699 B1 | 6/2002 | Ash |
| 6,416,293 B1 | 7/2002 | Bouchard et al. |
| 6,428,706 B1 | 8/2002 | Rosenqvist et al. |
| 6,755,976 B2 | 6/2004 | Rosenqvist et al. |
| 6,878,283 B2 | 4/2005 | Thompson |
| 7,033,498 B2 | 4/2006 | Wong |
| 7,077,956 B2 | 7/2006 | Rovatti |
| 7,241,272 B2 | 7/2007 | Karoor et al. |
| 7,947,179 B2 | 5/2011 | Rosenbaum et al. |
| 2002/0079695 A1 | 6/2002 | Campbell et al. |
| 2003/0105424 A1 | 6/2003 | Karoor et al. |
| 2004/0019312 A1 | 1/2004 | Childers et al. |
| 2004/0050789 A1 | 3/2004 | Ash |
| 2005/0274658 A1 | 12/2005 | Rosenbaum et al. |
| 2007/0158247 A1 | 7/2007 | Carr et al. |
| 2007/0158249 A1 | 7/2007 | Ash |
| 2007/0158268 A1 | 7/2007 | DeComo |
| 2007/0161113 A1 | 7/2007 | Ash |
| 2007/0161941 A1 | 7/2007 | Ash et al. |
| 2007/0181499 A1 | 8/2007 | Roberts et al. |
| 2008/0149563 A1 | 6/2008 | Ash |
| 2008/0177216 A1 | 7/2008 | Ash |
| 2009/0114595 A1 | 5/2009 | Wallenas et al. |

FOREIGN PATENT DOCUMENTS

| | | |
|---|---|---|
| EP | 1 342 480 | 9/2003 |
| EP | 1 096 991 | 6/2004 |
| WO | WO 97/02055 | 1/1997 |
| WO | WO 97/02056 | 1/1997 |
| WO | WO 98/17333 | 4/1998 |
| WO | WO 99/37342 | 7/1999 |
| WO | WO 02/30267 | 4/2002 |
| WO | WO 02/43859 | 12/2005 |
| WO | WO 2005/123230 | 12/2005 |
| WO | WO 2007/028056 | 3/2007 |
| WO | WO 2007/081383 | 7/2007 |
| WO | WO 2007/081384 | 7/2007 |
| WO | WO 2007/081565 | 7/2007 |
| WO | WO 2007/081576 | 7/2007 |

OTHER PUBLICATIONS

"*Sorbent Dialysis Pimer*," COBE Renal Care, Inc., Sep. 4, 1993 Ed.

Blumenkrantz et al., "*Artif Organs*," 3(3):230-236, 1978.

Operator's Manual—Fresenius 2008K Hemodialysis Machine (2000).

METHODS FOR CLEANING A DRAIN LINE OF A DIALYSIS MACHINE

TECHNICAL FIELD

The present invention relates generally to methods for cleaning a drain line of a dialysis machine.

BACKGROUND

Dialysis machines are used to cleanse the blood of medical patients suffering from kidney disease. A dialysis machine includes a blood pump and a blood filter (e.g., dialyzer) through which the blood flows to clean the blood. Arterial blood is drawn from the patient and delivered to the dialysis machine through external tubing. The arterial blood passes through the blood filter, and filtered blood is returned to the patient's venous system through other external tubing. The blood filter is provided with a measured amount of dialysate fluid via a separate dialysate fluid circuit. The dialysate fluid and the blood are separated by a membrane of the blood filter that allows the blood to be cleansed by the dialysate.

As part of the purification process, the dialysis machine incorporates a dialysate filtering system, which can be used to achieve ultrapure dialysate. After each treatment, the dialysate filtering unit is typically rinsed with purified water, which may be heated and may also include cleaning agents during part of the rinse cycle. It is also typically cleaned with a chlorine bleach solution about once per week, or sooner if the dialysis machine has not been used in more than about forty-eight hours. The water source and the bleach solution source are connected to the dialysate fluid circuit. The dialysate fluid circuit also includes a drain tube that empties spent fluid to a facility drain outside the dialysis machine.

SUMMARY

The invention, in one aspect, provides a method for cleaning a dialysate circuit downstream of a filtration unit in a dialysis machine. The dialysate circuit has a balancing chamber having a first part through which fresh, unused dialysate fluid passes to an inlet valve of a filtration unit via a source line. Spent dialysate fluid passes from the filtration unit via outlet valve to a drain line, which passes through a second part of the balancing chamber separated from the first part by a flexible diaphragm. A bypass line connects through a bypass valve between the source line and the drain line. The method includes: closing the inlet valve, the outlet valve, and the bypass valve; configuring the balancing chamber such that flow is permitted only via the drain line; flowing an amount of a cleaning agent into the drain line through a cleaning agent valve; and rinsing the cleaning agent from the drain line with a rinse fluid.

In one implementation, flowing the cleaning agent includes drawing the cleaning agent into the drain line with a pump positioned in the drain line between the balancing chamber and the cleaning agent valve. In another implementation, the pump is positioned between a source of the cleaning agent and the cleaning agent valve.

An amount of cleaning agent is flowed into drain line that is typically sufficient to fill the balancing chamber. This can be done by a timed flow, or alternatively by a direct measurement of the amount of cleaning fluid. The cleaning agent can be a sodium hypochlorite bleach solution, but other bleaches and cleaning and disinfecting agents can alternatively or additionally be used.

The process can be automated to be carried out upon initiation by an operator or at a set time of the day. It can also be carried out with more operator initiated steps.

Implementations of the invention may include one or more of the following advantages. By using certain methods described herein, the drain lines of a dialysis machine are kept cleaner, and thereby growth of protein slimes within the drain lines is inhibited. The methods, in some implementations, are easy for operators to carry out, and only take a few minutes for each cleaning cycle. In certain implementations, the drain lines are kept clean while the filtration unit is not subjected to excessive bleach treatments. In some implementations, very small quantities of cleaning agents are used, so the associated methods are cost effective, particularly when reduced major maintenance is taken into account.

Other aspects, features, and advantages of the invention will become more apparent from the following detailed description when taken in conjunction with the accompanying drawings.

DETAILED DESCRIPTION

Certain aspects of the invention described herein provide a simple and inexpensive system to clean a drain tube of a dialysis machine without exposing a dialysate filtering unit of the dialysis machine to a cleaning agent that is used to clean the drain tube.

Figure 1:
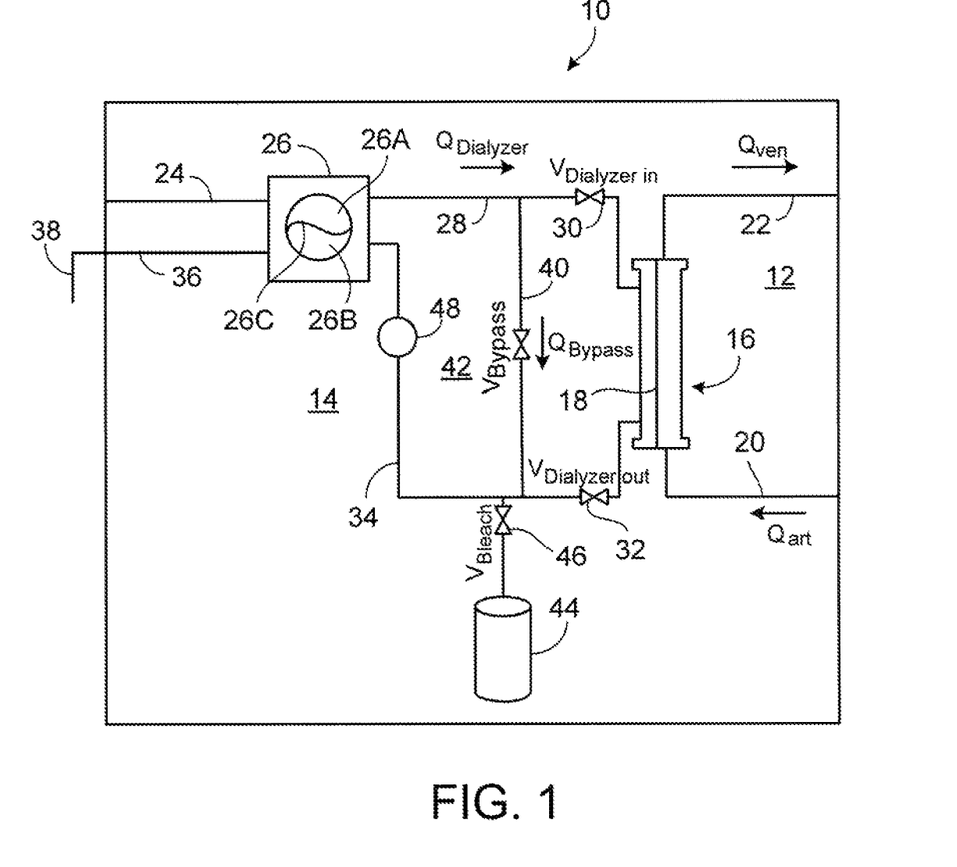
FIG. 1 is a simplified schematic diagram of the hydraulics of a dialysis machine according to an implementation of the invention.

Referring to FIG. 1, a dialysis machine 10 includes a blood circuit 12 and a dialysate fluid circuit 14 that each couple with a blood filtration unit (dialyzer) 16 having a semi-permeable membrane 18. The blood circuit 12 includes arterial flow tubing 20 that provides arterial blood from a patient during treatment to the filter unit 16, and venous flow tubing 22 that carries treated blood from the filter unit 16 back to the patient. The dialysate fluid circuit 14 includes a dialysate fluid source line 24 that provides dialysate fluid to a balancing chamber 26. The balancing chamber 26 provides a measured amount of dialysate fluid through source line 28 and inlet valve 30 to the filtration unit 16. Spent dialysate fluid is removed from the filtration unit 16 through outlet valve 32 and dialysate fluid drain line 34. The drain line 34 passes the spent dialysate fluid through the balancing chamber 26, from which it then passes through outlet drain line 36. Outlet drain line 36 then connects to a facility drain line 38 outside of the dialysis machine. There is also a bypass line 40 between source line 28 and drain line 34. Bypass valve 42 in bypass line 40 is normally closed during a patient treatment. There is also a bleach source 44 connected to drain line 34 through bleach valve 46, and a dialysate drain pump 48 between the bleach source 44 and the balancing chamber 26.

Traditionally, dialysis machine drain lines, such as drain lines 34, 36, 38, have been cleaned as part of a cleaning process used to clean the larger system. For example, a blood filtration unit, such as blood filtration unit 16, is typically cleaned with bleach after every thirteen dialysis treatments, or within 48 hours after the most recent treatment, and the drain lines, such as drain lines 34, 36, 38 are cleaned with bleach as part of this process. According to certain aspects of the invention, the drain lines 34, 36, and 38 receive an additional cleaning treatment (e.g., with a bleach solution) on a more frequent basis (e.g., daily) to inhibit the build-up of protein slime in these lines. These aspects of the invention generally provide for cleaning the portion of the dialysate circuit 14 downstream of the dialysate filtration unit 16. The balancing chamber 26 located along the dialysate circuit 14 has a first part 26A through which fresh, unused dialysate fluid passes to the inlet valve 30 of the filtration unit 16 via the source line 28. Spent dialysate fluid passes from the filtration unit 16 via the outlet valve 32 to the drain line 34, which is connected to a second part 26B of the balancing chamber 26. The first and second parts 26A, 26B of the balancing chamber 26 are separated from one another by a flexible membrane 26C. The bypass line 40 connects through the bypass valve 42 between the source line 28 and the drain line 34. The inlet valve 30, outlet valve 32 and bypass valve 42 are closed. The balancing chamber 26 is configured so that flow is permitted only via the drain lines 34, 36. Bleach is flowed into the drain lines 34, 36, 38 through the bleach valve 46, and then rinsed from the drain lines 34, 36, 38 with a rinse fluid flowing from the source lines 24, 28 and open valve 42 and/or open valves 30, 32.

Figure 2:
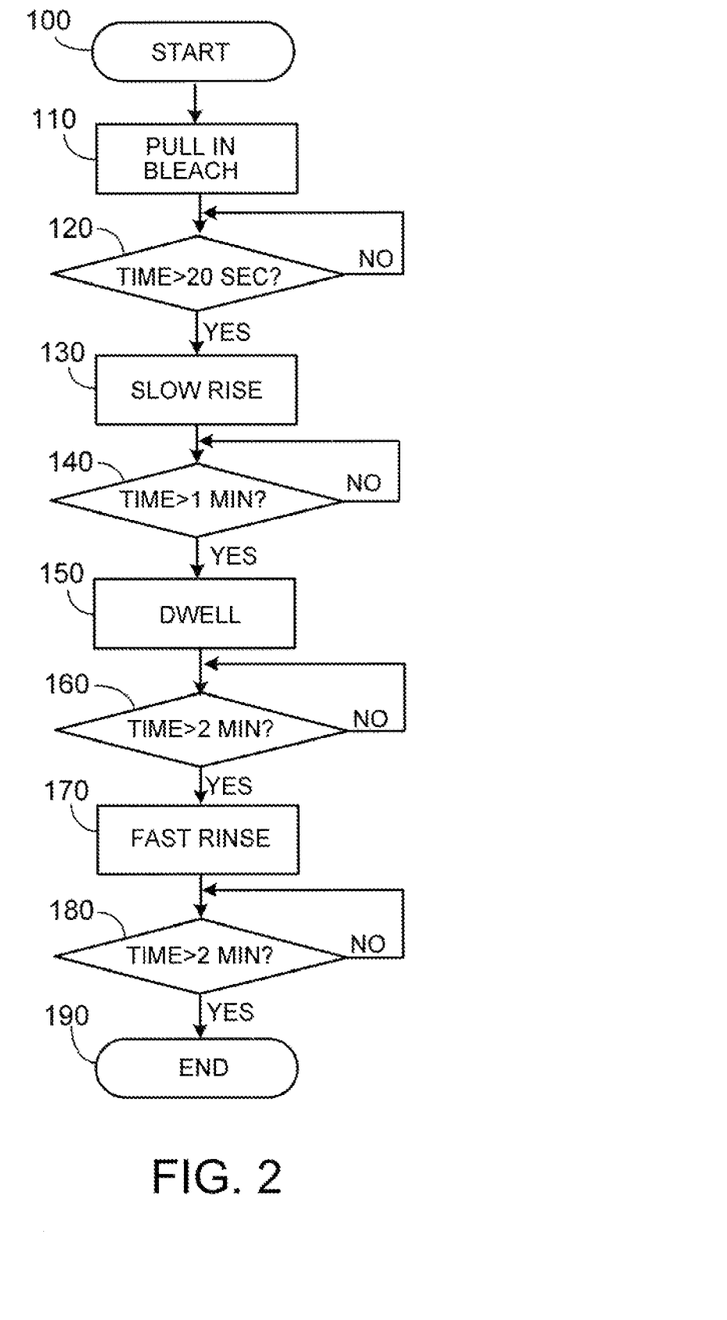
FIG. 2 is a flow diagram illustrating operation of the system shown in FIG. 1.

Referring now to FIG. 2, in one implementation of the invention, the drain cleaning cycle is a programmed operation of the dialysis machine 10 that the operator initiates (Start 100) with a switch, or a command through a user interface (not shown). Initiating the process starts a Pull in Bleach step 110. This step closes filtration unit inlet valve 30, outlet valve 32, and bypass valve 42. The balancing chamber 26 is set so that there is flow only to drain line 34. The bleach valve 46 is opened and the drain pump 48 is turned on. The drain pump 48 draws bleach from the bleach source 44 through line 34 and into the balancing chamber 26. The program checks if a first preset time period, e.g., 20 seconds, has elapsed 120 to allow a predetermined amount of bleach into the system. This preset amount is typically approximately the volume of the balancing chamber 26.

After the first preset time period has elapsed, the next programmed step is a Slow Rinse 130 of the drain line. With the drain pump 48 still on, bypass valve 42 is opened, bleach valve 46 is closed, and the balancing chamber 26 is set to flow for rinse, which allows a rinse fluid, e.g., purified water or unused dialysate fluid, to slowly flow from the dialysate fluid source line 24 through the balancing chamber 26, through source line 28 and bypass line 40, through the drain line 34, through the drain side of the balancing chamber 26, and on through drain lines 36 and 38. This continues for a second preset time period 140, e.g., 20 seconds, during which most of the bleach is flushed out of the drain lines 34, 36, 38. Alternatively, instead of rinsing through the bypass valve 42, the rinse can be done as in a normal cleaning procedure, by opening valves 30, 32 and flowing the rinse fluid through the filtration unit 16. After the second preset time, there is a Dwell step 150, wherein all valves are closed, the pump 48 is stopped, and the rinse fluid is allowed to dwell within the machine 10 and lines 24, 28, 34, 36, 38.

After a third set time 160, which may be approximately several minutes, the program initiates a Fast Rinse cycle 170. In this step, the rinse fluid is again drawn in to balancing chamber 26 and passes through source line 28, bypass line 40, and drain lines 34, 36, and 38. The Fast Rinse cycle 170 is set for a fourth time period 180 of sufficient duration to clear the lines of bleach and loosened debris. After the fourth time period has elapsed, the drain bleach cycle begins an End step 190. Pumps are turned off and the valves are positioned as they would be before initiating the next dialysis treatment.

Figure 3:
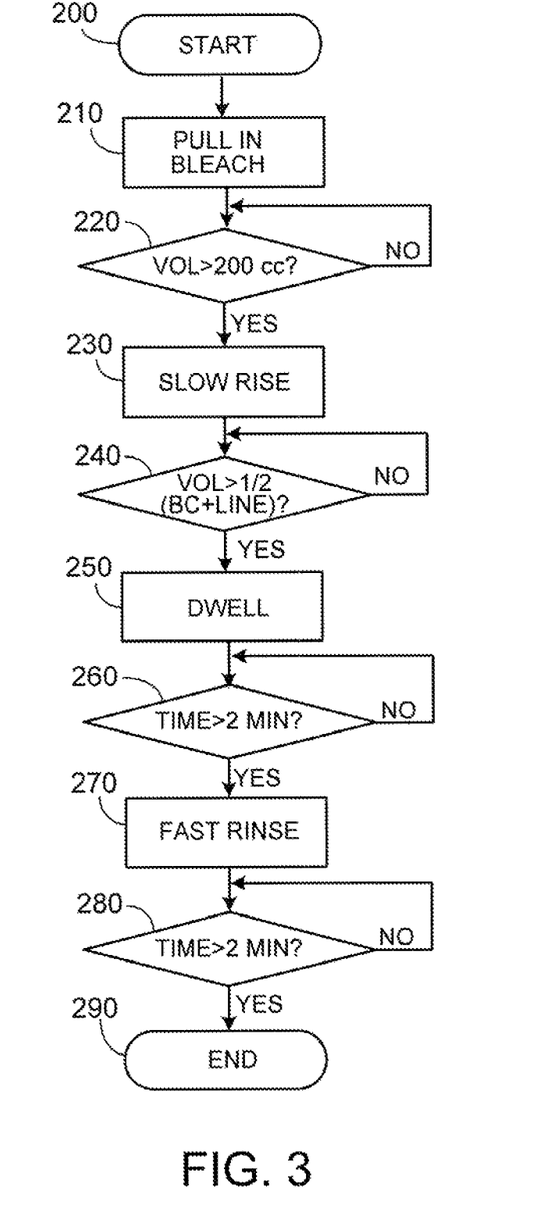
FIG. 3 is a flow diagram of an alternative method of operation.

In another implementation of the invention, illustrated by the flow diagram shown in FIG. 3, the bleach is metered out by volume rather than time. In this implementation, the operator starts the drain bleach cycle 200. The valves and pumps are set in the Pull in Bleach step 210 as in the previously described method (see Pull in Bleach step 110). The drain pump 48 draws bleach from the bleach source 44 through drain line 34 and into the balancing chamber 26. The program checks if a predetermined volumetric measurement 220 has been fulfilled (i.e., drawn). The set volume may be determined by the volume necessary to fill the balancing chamber and the drain lines (which can vary depending on the model of dialysis machine), or by some other volumetric aspect of the system. In the exemplary implementation, the predetermined volume is set at 200 cc.

When the set volume of bleach is reached, a Slow Bleach Rinse step 230 begins. This step is similar to the Slow Rinse step 130 described in the previous implementation, and circulates the bleach to the drain lines 34, 36 and to the drain line 38. The Slow Rinse step 230 stops when a sufficient volume is delivered 240. For example, as illustrated in the exemplary implementation of FIG. 3, the Slow Rinse step 230 may stop once the pump 48 delivers greater than half the volume of the balancing chamber plus the line. This begins the Dwell step 250, which ends after an elapsed set time 260, as in the previous implementation. Similarly, a Fast Rinse step 270 follows and ends after a predetermined time 280. The process has an End step 290, also as described in the previous implementation.

Figure 4:
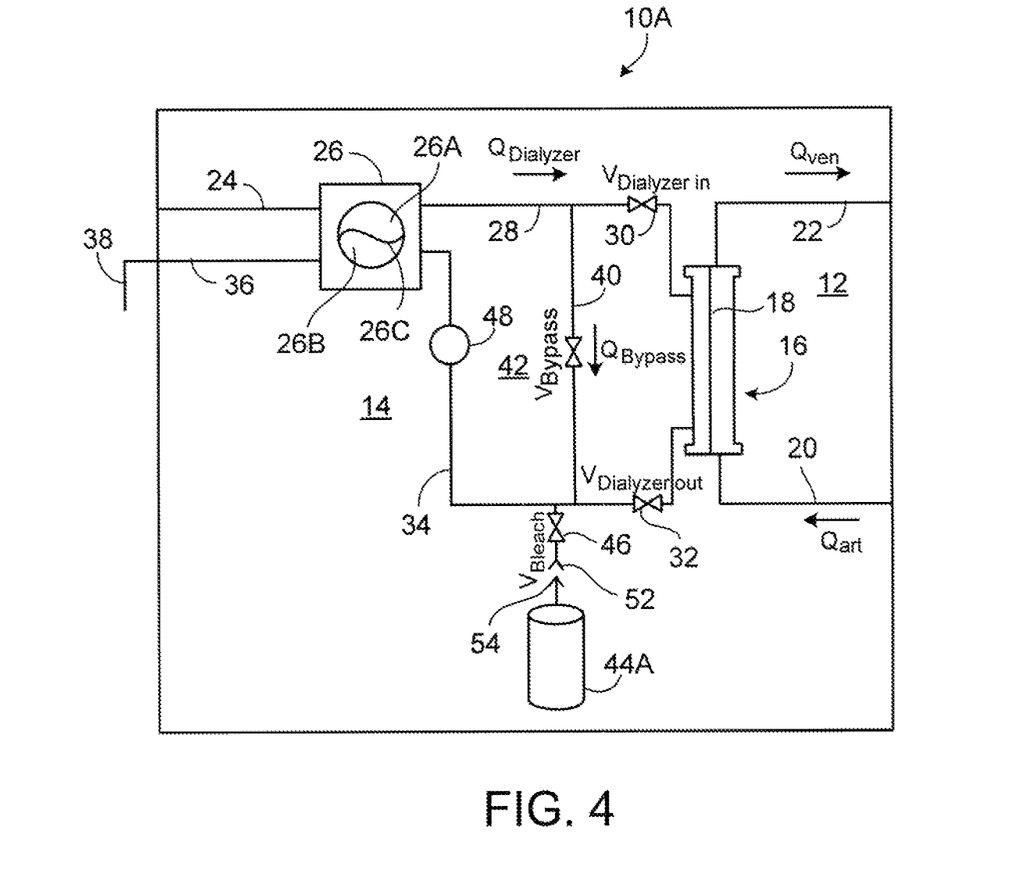
FIG. 4 is a simplified schematic diagram of the hydraulics of a second configuration of a dialysis machine.

In the cleaning apparatus and methods described above with reference to FIGS. 1-3, the bleach source 44 is a fixture in the dialysis machine 10. In an alternative arrangement illustrated in FIG. 4, a bleach source 44A is not a fixed component of a dialysis machine 10A, but rather is attached only when needed. In this arrangement, there is a fluid connector 52 at the inlet end of the bleach valve 46, which is adapted to connect with a mating fluid connector 54 on the bleach source 44A. This implementation can be operated by the methods described above with reference to FIGS. 2 and 3, however, the operator first must connect the bleach source 44A before starting the cleaning cycle. The bleach source 44A can remain connected until it needs to be replaced, or it can be removed in between drain line cleanings.

Figure 5:
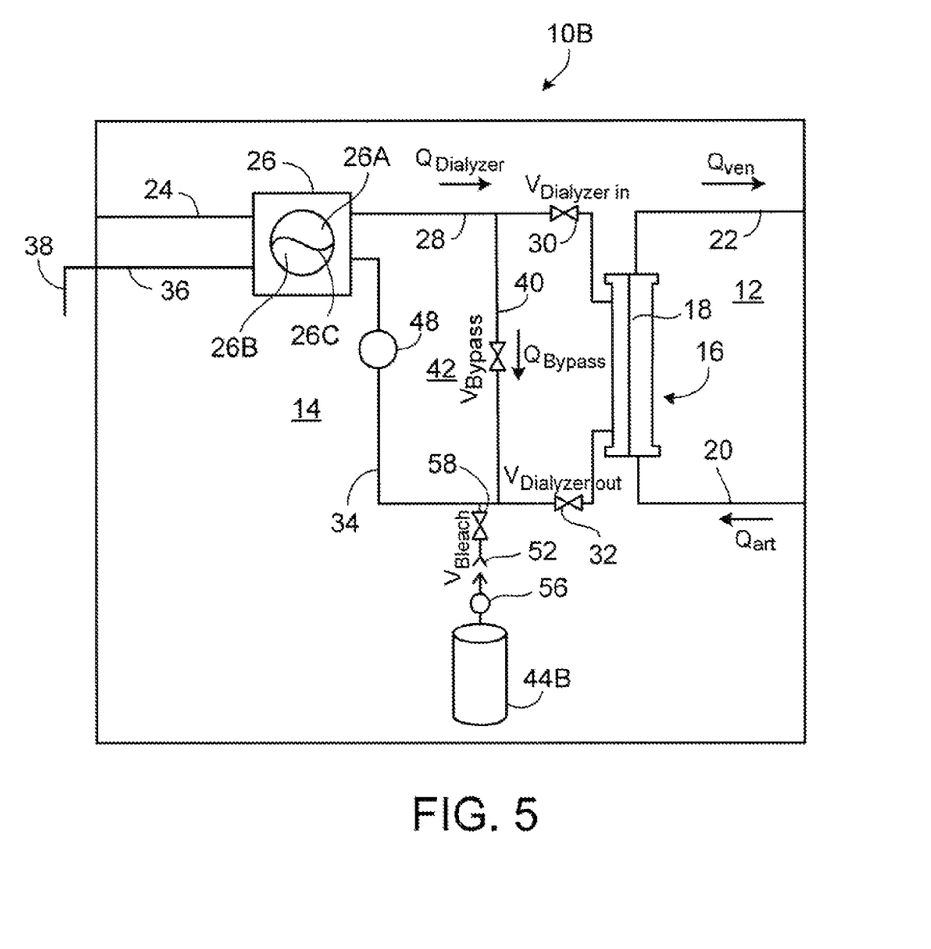
FIG. 5 is a schematic diagram of the hydraulics of a third implementation of a dialysis machine.

Another implementation of a dialysis machine configured for independent cleaning of the drain line is shown in FIG. 5. This implementation is similar to that illustrated in FIG. 4 in that a bleach source 44B is not a fixture of a dialysis machine 10B. However, in this implementation the drain line pump 48 is eliminated and instead there is a bleach pump 56 that is part of the removable bleach source 44B. This bleach pump 56, in combination with the balancing chamber 26, draws the bleach into the drain lines 34, 36, 38. Also shown in FIG. 5, the bleach valve 46 may be replaced with a less expensive check valve 58. These configurations have the advantage of being simple to adapt to dialysis machines already in use.

Figure 6:
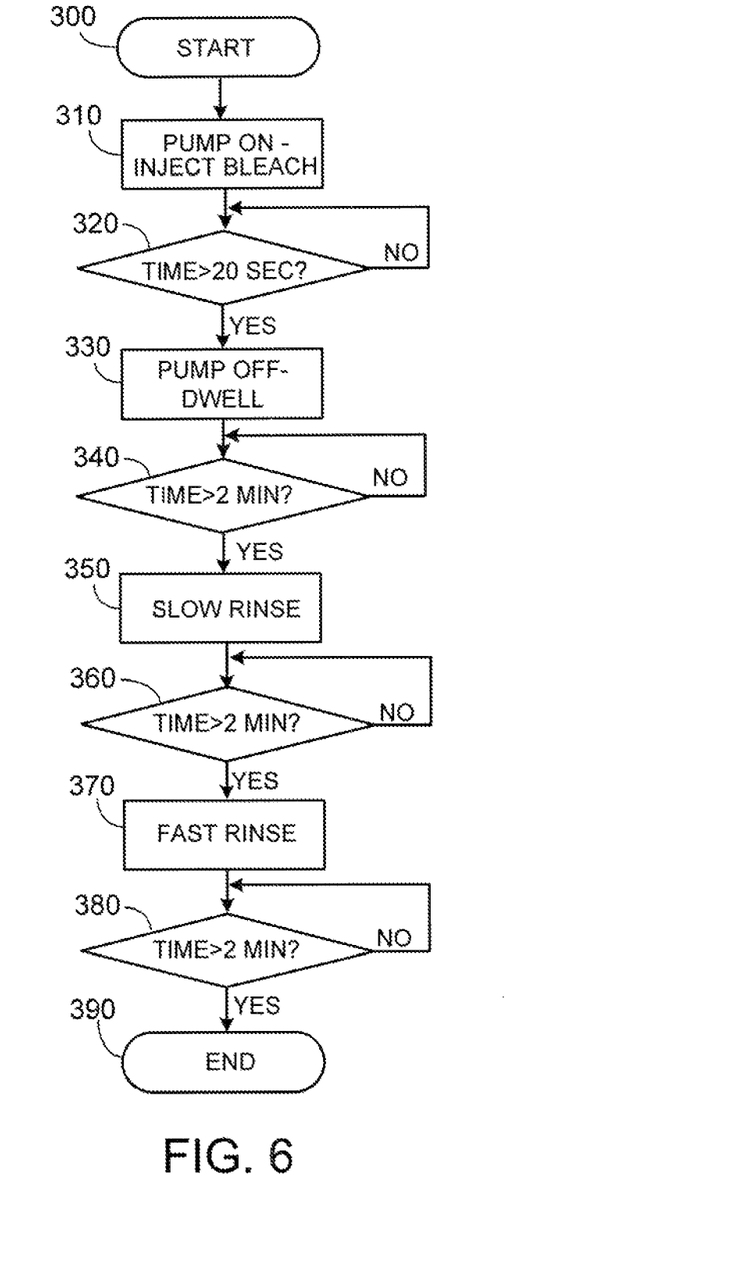
FIG. 6 is a flow diagram illustrating operation of the system shown in FIG. 5.

A method of operation of the system shown in FIG. 5 is illustrated by FIG. 6. In the Start step 300, the operator connects the bleach source 44B to the dialysis machine 10B by connecting fluid connectors 52 and 54. Valves 30, 32, and 40 are closed and the balancing chamber is set so that there is flow only to the drain line. The operator then turns Pump On 310, which injects bleach into drain line 34. After a first time period 320, e.g., at least about 20 seconds, the operator turns the Pump Off 330. The pump remains off for a second time period 340, e.g., about 2 minutes. The operator then initiates a Slow Rinse cycle 350, which lasts for a third time period 360, e.g., about 2 minutes, and then a Fast Rinse 370, which lasts for a fourth period of time 380, e.g., about 2 minutes. After the Fast Rinse 370, the cleaning process ends 380.

The specific devices and methods described above may utilize a chlorine bleach solution (sodium hypochlorite) as the cleaning and disinfecting agent. The rinse used to remove the bleach or other cleaning agent can be a dialysate fluid, purified water, or any other rinse commonly used for dialysis machines.

While the apparatus and methods above have been described as using bleach to clean the drain lines, other cleaning and disinfecting agents may alternatively or additionally be used. For example, detergents, surficants, and enzymes, alone or in combination with each other, can be used as an alternative to or in addition to bleach.

While certain implementations of the invention have been described, other implementations are within the scope of the following claims.

What is claimed is:

1. A method for cleaning a dialysate circuit downstream of a filtration unit in a dialysis machine, wherein the dialysate circuit includes a balancing chamber through which (a) unused dialysate fluid passes to an inlet valve of a filtration unit via a source line, and (b) spent dialysate fluid passes from an outlet valve of the filtration unit via a drain line, and a bypass line connecting through a bypass valve between the source line and the drain line, the method comprising:

closing the inlet valve, the outlet valve, and the bypass valve;

configuring the balancing chamber such that flow is permitted only via the drain line;

flowing an amount of a cleaning agent into the drain line through a cleaning agent valve; and rinsing the cleaning agent from the drain line with a rinse fluid.

2. The method of claim 1, wherein flowing the cleaning agent includes drawing the cleaning agent into the drain line with a pump positioned in the drain line between the balancing chamber and the cleaning agent valve.

3. The method of claim 1, wherein flowing the cleaning agent includes filling the balancing chamber with the cleaning agent.

4. The method of claim of claim 1, wherein flowing the cleaning agent includes flowing a measured amount of cleaning agent.

5. The method of claim 1, wherein flowing the cleaning agent includes flowing the cleaning agent for a predetermined period of time.

6. The method of claim 1, wherein rinsing includes rinsing with dialysate fluid.

7. The method of claim 1, wherein rinsing includes rinsing with water.

8. The method of claim 1, wherein rinsing includes a first and second rinse.

9. The method of claim 1, wherein the cleaning agent is a chlorine bleach.

10. The method of claim 9, wherein the chlorine bleach is a sodium hypochlorite solution.

11. The method of claim 1, wherein the cleaning fluid includes at least one member selected from the group consisting of: bleaches, detergents, bactericides, enzymes, and surfactants.

12. The method of claim 1, wherein rinsing includes opening the bypass valve.

13. The method of claim 1, wherein rinsing includes opening the inlet valve and the outlet valve so the rinse fluid passes through the filtration unit prior to rinsing the drain line.

\* \* \* \* \*